United States Patent [19]

Mortara

[11] Patent Number: 4,951,681

[45] Date of Patent: Aug. 28, 1990

[54] ELECTROCARDIOGRAPHIC RECORDING METHOD AND APPARATUS

[75] Inventor: David W. Mortara, River Hills, Wis.

[73] Assignee: Mortara Instrument, Milwaukee, Wis.

[21] Appl. No.: 271,106

[22] Filed: Nov. 14, 1988

[51] Int. Cl.[5] .............................................. A61B 5/04
[52] U.S. Cl. ..................................... 128/710; 346/136
[58] Field of Search .................. 128/710; 346/33, 136; 318/490

[56] References Cited

U.S. PATENT DOCUMENTS

| 3,908,641 | 9/1975 | Judson et al. | 128/710 |
|---|---|---|---|
| 4,038,666 | 7/1977 | Fuller, Jr. | 346/136 |
| 4,100,470 | 7/1978 | Andrews | 346/136 |
| 4,184,487 | 1/1980 | Peyer | 128/710 |
| 4,214,590 | 7/1980 | Patnoi et al. | 346/136 |
| 4,215,351 | 7/1980 | Lowe | 346/136 |
| 4,222,057 | 9/1980 | Cuvelier | 346/33 |
| 4,417,254 | 11/1983 | Woods | 346/136 |
| 4,509,530 | 4/1985 | Curtis et al. | 128/710 |
| 4,628,233 | 12/1986 | Bradus | 318/490 |
| 4,628,327 | 12/1986 | Anderson et al. | 128/710 |

Primary Examiner—Francis Jaworski
Assistant Examiner—George Manuel
Attorney, Agent, or Firm—Godfrey & Kahn

[57] ABSTRACT

Disclosed herein is a method and apparatus employing a D.C. drive motor and digital printhead for recording electrocardiographic data or other digital data on a chart at a constant time scale, regardless of temporary variations in the D.C. motor speed. A buffer memory stores sensed digital ECG data, and a data count register provides a count indicative of the amount of data stored. A pulse width register controls the width of long and short pulses generated by a motor driver for the selected paper speed. An experience count register has a count indicative of the relative number of long and short pulses generated. The original or current width of the pulses may be adjusted by the pulse width register, subject to the count of the experience count register, for controlling the speed of the D.C. drive motor. The motor speed is increased if the buffer memory is storing more than a preselected amount of data, and the motor speed is decreased if the buffer memory is storing less than a preselected amount of data. Means, including a tach count register, regulate the output of ECG data from the buffer memory to the digital printhead for recording at a rate proportional to the speed of the D.C. drive motor, to produce a constant time scale chart record of such data, regardless of temporary variations in the D.C. motor speed.

31 Claims, 2 Drawing Sheets

| 25 MM / SEC | | |
|---|---|---|
| TACH COUNT | TIME | TIME − P TIME |
| 0 | 0 | 0 |
| 1 | 0 | 0 |
| 2 | 1 | 1 |
| 3 | 2 | 1 |
| 4 | 3 | 1 |
| 5 | 4 | 1 |
| 6 | 4 | 0 |
| 7 | 5 | 1 |
| 8 | 6 | 1 |

FIG. 3b

| 50 MM / SEC | | |
|---|---|---|
| TACH COUNT | TIME | TIME − P TIME |
| 0 | 0 | 0 |
| 1 | 0 | 0 |
| 2 | 0 | 0 |
| 3 | 1 | 1 |
| 4 | 1 | 0 |
| 5 | 2 | 1 |
| 6 | 2 | 0 |
| 7 | 2 | 0 |
| 8 | 3 | 1 |
| 9 | 3 | 0 |
| 10 | 4 | 1 |

FIG. 3c

| 5 MM / SEC | | |
|---|---|---|
| TACH COUNT | TIME | TIME − P TIME |
| 0 | 0 | 0 |
| 1 | 4 | 4 |
| 2 | 8 | 4 |
| 3 | 12 | 4 |
| 4 | 16 | 4 |
| 5 | 20 | 4 |

# 4,951,681

ELECTROCARDIOGRAPHIC RECORDING METHOD AND APPARATUS

BACKGROUND OF THE INVENTION

The present invention relates to a method and apparatus employing a D.C. drive motor and a digital printhead for graphically recording electrocardiographic data on a constant time scale chart record.

It is known to utilize a D.C. drive motor in portable monitoring equipment, such as an electrocardiogram (ECG) so that such portable equipment is of a relatively small size and low weight. There are, however, inherent difficulties with maintaining a constant motor speed and constant time scale when a D.C. motor is employed to drive a strip chart of an ECG. For example, there can be momentary changes in motor speed as a result of change of the load on the motor relating to paper friction or inconsistencies in the paper feed characteristics of the paper roll utilized.

Generally, in prior art portable recorders, the D.C. motor speed may be regulated to maintain a generally constant speed in response to changes on the load of the D.C. motor, but such speed regulation arrangements require additional circuitry which adds to the complexity and expense of such equipment. Typically, such prior art recorders compensate for changes in the load on the D.C. motor to attempt to maintain a constant D.C. motor speed, and data is delivered for recording at a set rate to attempt to provide a constant time scale chart record. The compensation for changes in the load of the D.C. motor are not instantaneous, however, given the mechanical reaction time of the motor and speed regulation arrangements, so that there will be momentary variations in motor speed, which when data is delivered for recording a set rate, results in the recorder failing to provide a uniform constant time scale chart record.

Attention is also directed to the following U.S. patents:

| Patentee | Patent No. | Issue Date |
| --- | --- | --- |
| E. G. Fuller, Jr. | 4,038,666 | 07/26/77 |
| Andrews | 4,100,470 | 07/11/78 |
| Patnoi et al | 4,214,590 | 07/29/80 |
| Lowe | 4,215,351 | 07/28/80 |
| Cuvelier | 4,417,057 | 09/09/80 |
| Woods | 4,417,254 | 11/22/83 |

SUMMARY OF THE INVENTION

The present invention overcomes the difficulties of the prior art by providing a method and apparatus employing a D.C. drive motor and digital printhead wherein sensed digital ECG data is stored in a buffer memory and the preselected nominal speed of the D.C. motor is controlled in accordance with the amount of data stored in the buffer memory, and outputting of digital data to the printhead from the buffer memory occurs at a rate proportional to the speed of the D.C. drive motor, so as to produce a constant time scale chart record, regardless of temporary variations in the D.C. motor speed.

In one embodiment of the invention, the method includes the steps of storing sensed digital ECG data by means of a buffer memory, controlling the speed of the D.C. drive motor in accordance with the amount of data stored in the buffer memory, so that the motor speed is increased if the buffer memory is storing more than a preselected amount of data, and so that motor speed is decreased if the buffer memory is storing less than the preselected amount of data, and outputting ECG data from the buffer memory to the printhead for recording at a rate proportional to the speed of the D.C. drive motor, so as to produce a constant time scale chart record of such data regardless of temporary variations in the D.C. drive motor speed.

In a preferred embodiment of the invention, the steps for controlling the speed of the D.C. drive motor are further defined as utilizing a data count register and a pulse width register, and adjusting the data count register to have a count indicative of the amount of data contained in the buffer memory, and controlling the pulse width register to effect generation of, during a given time interval, a long pulse to energize the D.C. motor if the count of the data count register is greater than the preselected value, or a short pulse to energize the D.C. motor if the count of the data count register is less than the preselected value.

In a preferred embodiment of the invention, the step for controlling the speed of the D.C. drive motor is further defined as utilizing an experience count register, and incrementing by a fractional value the experience count register each time a long pulse is generated, and decrementing by a fractional value the experience count register each time a short pulse is generated and, when the experience count register reaches a positive integer value, adjusting the pulse width register to increase the width of the long and short pulses generated, to increase the speed of the D.C. motor, and when the experience count register reaches a negative value, adjusting the pulse width register to decrease the width of the long and short pulses generated, to decrease the D.C. motor speed.

In a preferred embodiment of the invention, the step of adjusting the data count register is further defined as incrementing the count of the data count register in response to a piece of data being stored in the buffer memory per a given unit of time. The step of outputting data is further defined as utilizing a tach count register, and incrementing the count in the tach count register upon the occurrance of a tach pulse generated by the D.C. motor, and calculating upon the occurrance of a tach pulse a "TIME" value equal to the count in the tach count register, divided by the number of tach pulses per such given unit of time, the quotient being rounded to the smallest whole number. If "TIME" is greater than "PTIME", where "PTIME" is equal to the last value of "TIME" prior to the tach count register being incremented by an additional tach pulse, (TIME−PTIME) is subtracted from the value of the data count register and data is output from the buffer memory to the printhead for recording. Preferably, the step of outputting data from the buffer memory is further defined as outputting from the buffer memory to the printhead for recording a piece of data located in the buffer memory at a point corresponding to the resulting count of the data count register after subtraction of (TIME−PTIME).

As explained herein, the subject invention also provides a method and apparatus employing a D.C. drive motor and means for supplying digital data in a recorder other than an ECG for graphically recording other types of data on a constant time scale, regardless of temporary variations in the D.C. drive motor speed.

One of the principal features of the invention is the provision of a method and apparatus as described above, wherein temporary variations in the D.C. motor speed do not interfere with providing a constant time scale chart record, since outputting of the data from the buffer memory occurs at a rate proportional to the speed of the D.C. motor. In such arrangement, the buffer memory absorbs and retains data while the output of the data from the buffer memory is slowed in response to a temporary slowing of the D.C. motor speed, and the buffer memory outputs data for recording at an increased rate in response to a temporary increase in the D.C. motor speed, to thereby maintain a constant time scale chart record regardless of such temporary variations in motor speed.

Other features and advantages of the embodiments of the invention will become known by reference to the following general description, claims and drawings.

Before explaining the preferred embodiment of the invention in detail, it is to be understood that the invention is not limited in its application to the details of construction and arrangement of components set forth in the following description or illustrated in the drawing. The invention is capable of other embodiments and being practiced and being carried out in various ways. Also, it is to be understood that the phraseology and terminology employed herein is for the purpose of description and should not be regarded as limiting.

DETAILED DESCRIPTION OF THE PREFERRED EMBODIMENT

Figure 1:
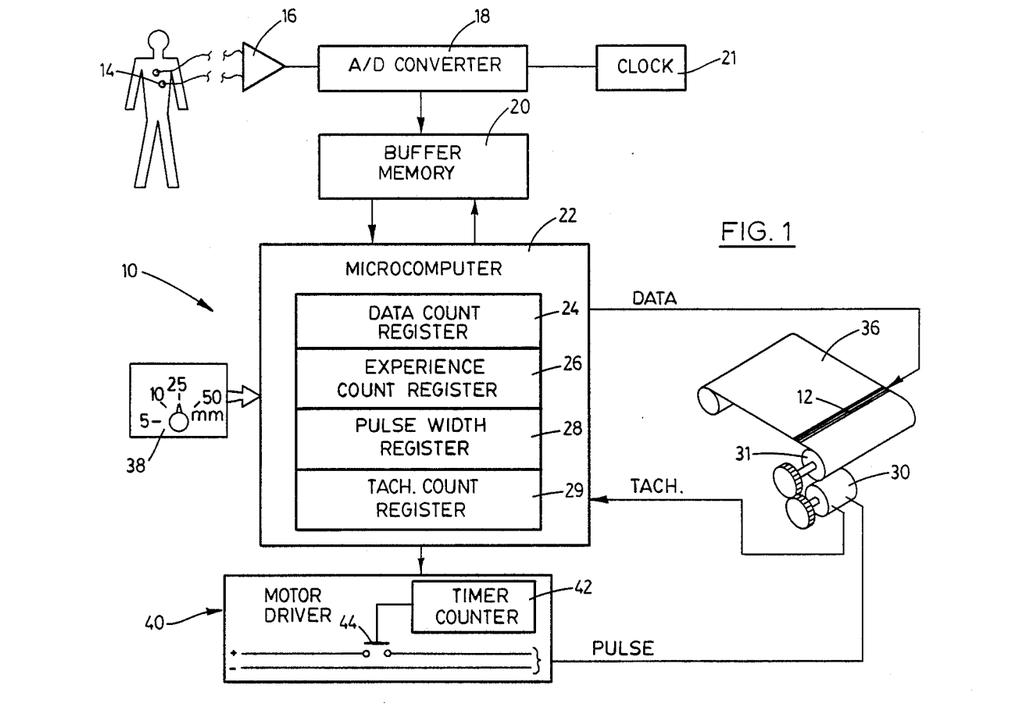
FIG. 1 is a schematic block diagram of an electrocardiogram which illustrates an embodiment of the present invention.

Analog data is processed by an electrocardiograph (ECG), generally designated 10, embodying the subject invention, and plotted by a suitable digital thermal printhead 12, such as can be obtained from Kyocera of Japan, Part No. KST-216-8MPDI. The analog data is provided by source 14 which provides signals to amplifier 16, in turn supplied to analog to digital converter 18 which, in customary fashion, converts data to digital form, which is supplied at a given frequency, preferable at a rate of one piece of data per millisecond, to buffer memory 20, subject to control of clock 21. The output of buffer memory 20 is connected to a microcomputer, generally designated 22, which is made up of suitable ROM and RAM components and a microprocessor (not specifically shown). A suitable microprocessor can be obtained from Motorola as Part No. HC68000, which in turn operates with commercially available ROM and RAM components. The microcomputer 22 includes a data count register 24, an experience count register 26, a pulse width register 28, and a tach count register 29, whose functions will be described in more detail below. While shown as separate components for clarity, the buffer memory is provided by the RAM of the microcomputer 22, and the clock 21 is derived in customary fashion from an internal 10 megahertz clock (not shown) contained within the microcomputer 22.

The ECG 10 also includes a D.C. drive motor 30, which conventionally includes an internal gear reduction and has an output shaft which is coupled in customary fashion by gears to a platen 31, which drives the chart paper 36 from a paper roll past the printhead 12. The D.C. drive motor 30 generates a tach signal, which in the preferred embodiment, corresponds to 20 microns of chart paper travel per tach pulse. A suitable D.C. motor can be obtained from Micro Mo Electronics of St. Petersburg, Fla., Motor Part No. 1624EO12567-123. The microcomputer 22 processes the tach pulses from motor 30, for controlling output from the buffer memory 20 to the printhead 12, as will be described in more detail below.

The user selected "speed" of the D.C. drive motor 30 is specified in millimeters of paper passing past the printhead per second, for example, 25 mm/sec. The user selects the chart paper speed by a speed control diagramatically shown as 38, which causes adjustment of the pulse width register 28 of the microcomputer 22, to control a motor driver 40, which couples a suitable D.C. power source, such as an 18 volt lead/acid battery, to the D.C. motor 30, to deliver a combination of "long" and "short" pulses to the motor. While other arrangements are possible, in the preferred embodiment, as will be described in connection with the flow chart shown in FIG. 2, a long or short pulse is delivered at one millisecond intervals to cause motor rotation and provide for the selected nominal chart paper speed.

The motor driver 40 includes a timer/counter 42 which controls a switch 44 for connecting the D.C. source to the motor 30 to deliver the long and short pulses and energize the motor. The timer/counter 42 is controlled by the pulse width register 28 and counts down to zero using clock "units" of the 10 megahertz microcomputer clock (i.e. 10,000 ticks divided by 256, as discussed below) so that the switch 44 is closed when the count of the timer/counter 42 is greater than zero and so that the switch 44 is open when the count of the timer/counter 42 reaches zero. A suitable commercially available timer/counter for use in motor driver 40 can be obtained from NEC, Part No. 71054.

During motor start-up, the microcomputer 22, during a start-up routine, adjusts the pulse width register 28 which causes the motor driver 40 to provide increased width pulses so that the motor 30 achieves its nominal selected speed within a period of, for example, 128 milliseconds. Therfter, initial settings of pulse widths for selected speeds are provided as follows.

As previously noted, the microcomputer 22 includes an internal 10 megahertz clock (not shown) which provides 10,000 ticks per millisecond, this being the maximum pulse width during a 1 millisecond interval. In the preferred embodiment, and for purposes of example, the 10,000 ticks is divided by 256 to provide approximately 39 "units" of pulse width available during a given millisecond interval. The pulse width register 28 is set, and controls the motor driver 40, so that the initial pulse widths provided, for example, at a user selected speed of 25 mm/sec., are a 14 "unit" pulse width corresponding to a "short pulse", and a 22 "unit" pulse width corresponding to a "long pulse". The pulse width register is set and controls the motor driver 40, so that other nominal values for short and long pulse widths for other user selected speeds are, for example, at 5 mm/sec., 6 units for a short pulse and 12 units for a long pulse, at 10 mm/sec., 10 units for a short pulse and 16 units for a long pulse , and at 50 nm/sec., 24 units for a short pulse and 32 units for a long pulse. During operation, the initial or current pulse widths are adjusted by additional "unit" increments, to maintain the proper motor speed as will be described in connection with the logic routine shown in FIG. 2.

Figure 2:
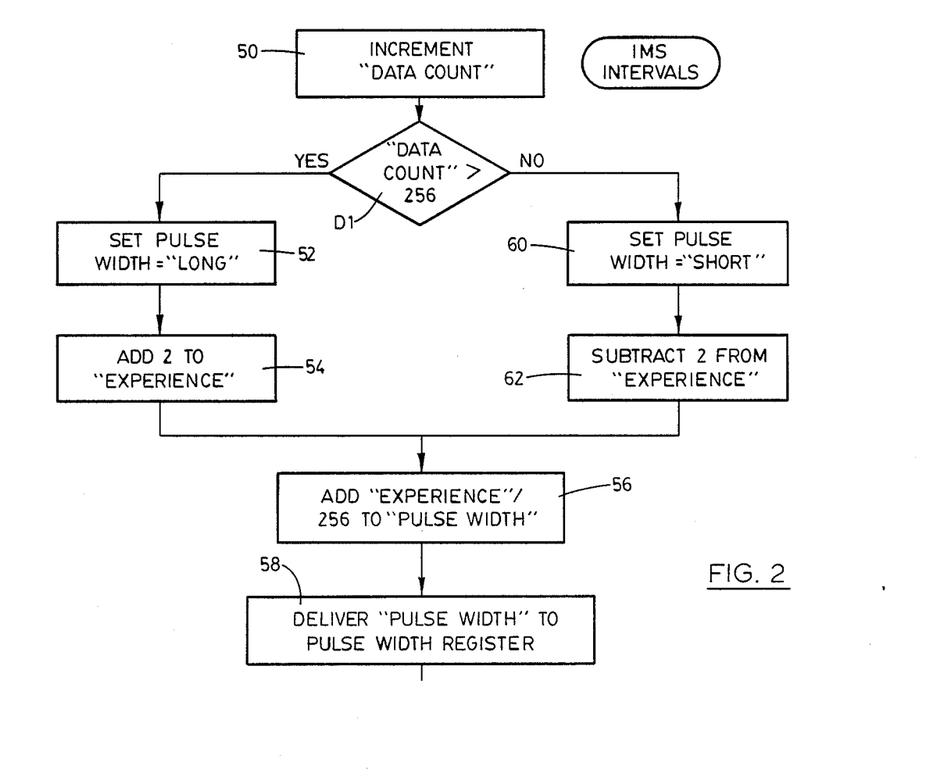
FIGS. 2 and 3 are flow diagrams of the operation of the microcomputer shown in FIG. 1.

Referring to the flow chart shown in FIG. 2, the following is a description of the logic routine of the microcomputer 22, repeated at one millisecond intervals, to control the speed of the D.C. motor in accordance with the amount of data stored in the buffer memory 20. Basically, a decision will be made every millisecond as to whether a "long" pulse width or a "short" pulse width should be supplied to the motor 30 to maintain the speed of the motor 30 at a preselected nominal value corresponding to the user selected paper speed, for example 25 millimeters per second. Subject to the clock 21, data or a digital word is added to the buffer memory 20 at millisecond intervals, and in a corresponding fashion, the clock 21 increments or adds one to the data count register 24, as indicated at block 50. While different values could be utilized, the data count register has a nominal count value of 256 after motor start-up, corresponding to the buffer memory 20 being set to output the last 256 pieces of data accumulated during motor start-up. The last 256 pieces of data stored in the buffer memory 20, which will be outputted on a first-in first-out basis, corresponds to about a ¼ second delay before any data is outputted to the printhead, as will be described below in connection with the flow chart shown in FIG. 3.

Referring to FIG. 2, whether or not the value of the data count register is greater than 256 is made by a decision $D_1$. If the answer is "YES", as would be the case if the data count and the amount of data stored in the buffer memory 20 exceeds the nominal preselected value of 256, a long pulse width will be selected at block 52, and the motor speed is increased. Also, a value of "2" will be added to the experience count register 26 as indicated at block 54. The count of the experience count register, divided by 256, is then added to the pulse width register 28, as indicated at block 56, as follows. When the value of the experience count register divided by 256, (the microcomputer logic rounds down to the smallest whole number) is equal to one or a larger integer, the integer value is added to increment the "unit" pulse widths of the pulse width register 28, as indicated at block 58, to thereby compensate and increase the original or current width of the long and short pulses generated by the motor driver 40 for a given selected chart paper speed.

Dividing the value of the experience count register by 256 at block 56 functions to prevent undue motor speed oscillation. For example, if the motor speed is too slow and the routine produces only long pulses, this will occur for 128 milliseconds or about ⅛ of a second, before the experience count register reaches a positive integer value of one, and the pulse width register is incremented to add one "unit" to the original unit widths of the pulses produced by the motor driver 40. In effect, per the example given, when the number of long pulses exceeds the number of short pulses by a given value, in this case 128, the value of the experience count register equals 1 and the original or current width of the long and short pulses is increased by one "unit", to increase the motor speed. This routine and compensation of motor speed by adjustment of the original or current pulse widths will continue, tending to regulate the speed of the motor so that the count of the data count register 24 and the amount of data stored in the buffer memory 20 moves slowly above and below the preselected value of 256, as the correct motor speed is generally maintained. This compensation of motor speed will be effective, even for what may be described as "long term" variations in the load on the D.C. motor which could, for example, be due to a change in paper drag or friction resulting from use of a different size or type of paper roll. This compensation of motor speed will also be effective in response to changes in the voltage level of the D.C. battery supplying the D.C. motor.

Returning to operation of the routine, if at decision $D_1$ the answer is "NO", as would be the case if the data count and the amount of data stored in the buffer memory 20 is less than the nominal preselected value of 256, a "short" pulse width will be selected at block 60 and the motor speed is decreased, as a result of receiving a short rather than long pulse width during such millisecond interval. Also, "2" will be subtracted, rather than added, to the experience count register 28 as indicated at block 62.

In the same way that a positive count of 256 in the experience count register will result in increasing the current or original pulse width as described above to increase motor speed, a negative count in the experience count register, resulting from subtraction, will result in compensating and decreasing the current or original pulse widths at blocks 56 and 58 to decrease the speed of motor 30, until the value of the data count register and the amount of data stored in the buffer memory 20 increases to again move slowly above and below the preselected value, to maintain the correct motor speed.

As discussed above, there may be situations where there will be an approximate ⅛ second delay before the experience count register causes the pulse width register to add or subtract a unit to the initial or current pulse widths to further compensate for what may be a temporary change in the load on the D.C. motor. Such temporary changes may result, for example, due to an increase or decrease of friction encountered during delivery of paper from the paper roll. Such situations could result in temporary variations of motor speed, for example, lasting on the order of ⅛ to ¼ second. In accordance with the method and apparatus of the present invention, such temporary variations in motor speed will not interfere with providing a constant time scale chart record, since outputting of the data from the buffer memory occurs at a rate proportional to the speed of the D.C. drive motor. The buffer memory 20 has the ability to, in effect, absorb and retain data while the output of data from the buffer memory is slowed in response to a temporary slowing of the motor speed, and to output data for recording at an increased rate in response to a temporary increase in the speed of the motor, to maintain a constant time scale chart record, as further discussed below. The buffer memory 20 preferably should have a storage capacity greater than twice the amount of storage required for the last 256 pieces of data accumulated during motor start-up, to accomodate absorbing and retaining a comparable amount of additional data while the output of data from the buffer memory may be slowed in response to a temporary slowing of the motor speed.

Figure 3:
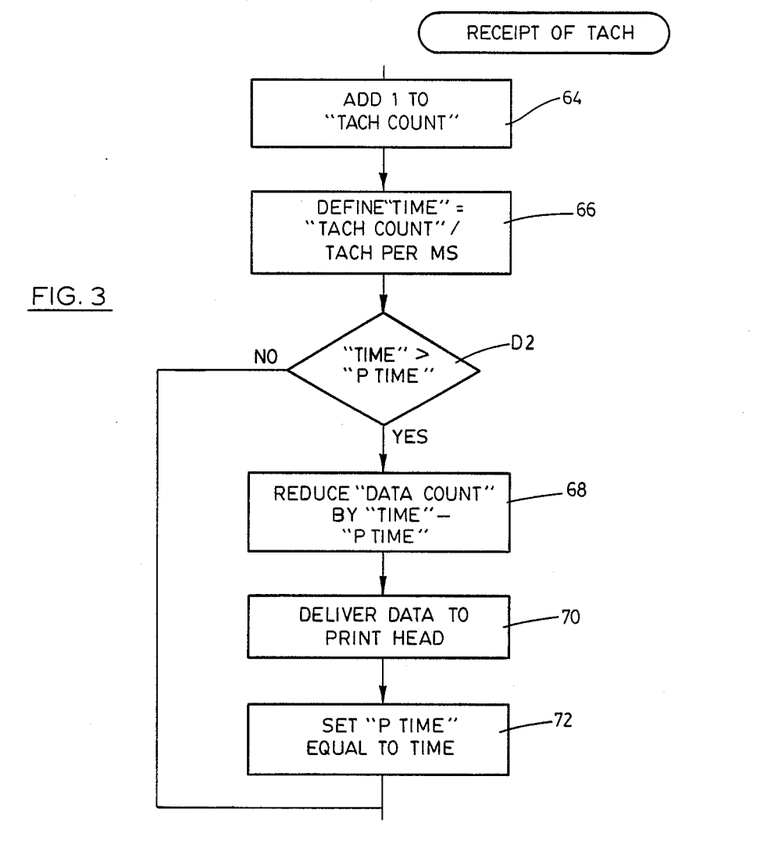

A description of the logic routine which results in outputting data from the buffer memory 20 to supply digital ECG signals to the printhead 12, at a rate proportional to the speed of the D.C. drive motor 30, will now be given with reference to FIG. 3. A piece of data is outputted to the printhead 12 from the buffer memory means 20 as a result of a command from the microcomputer 22, which is tach pulse driven. The logic routine is illustrated in the flow chart shown in FIG. 3. For ease of explanation, this description will assume the value of the tach count register is initially 0. Upon receipt of a tach pulse from motor 30, 1 is added to the tach count register 29 as indicated at block 64.

As represented by block 66, "TIME" is defined to be "TACH COUNT" divided by tachs per a given unit of time, one millisecond, in the preferred embodiment described herein. Also, as previously referenced, in the preferred embodiment, a tach pulse is produced by motor 30 for every 20 microns of movement of chart paper. At a selected speed of 25 mm/sec., which equates to 25 microns per millisecond, there will be 1.25 tach pulses per millisecond. Thus, initially, with a tach count of 1, TIME is equal to 1 tach count divided by 1.25 tachs per millisecond, or 0, since only integer values produced at block 66 are recognized by the logic of microcomputer 22. Whether or not "TIME" is greater than "PTIME" (which is defined and set to be the immediately preceding TIME value) is made by decision $D_2$. Since TIME is not greater than PTIME, the answer is "NO" and the routine repeats upon receipt by the tach count register 29 of another tach signal. The next routine results in TIME being equal to 1 (2 divided by 1.25) and therefor TIME is greater than PTIME (0), so the answer at decision $D_2$ is "YES".

Figure 3A:
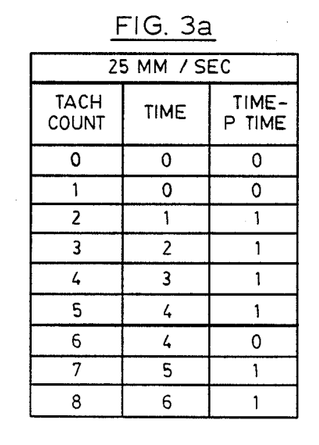
FIGS. 3(a), (b) and (c) are tables of values, at different selected paper chart speeds, to assist in explanation of the flow chart shown in FIG. 3.

As indicated at block 68, the data count register is reduced by (TIME−PTIME) or 1. As designated by block 70, the microcomputer 22 correspondingly causes one piece of data to be outputted from the buffer memory 20 to the printhead 12. To complete the routine, "PTIME" is set to the value of TIME. Thus, upon receipt of the next tach pulse, TIME=2 (3 divided by 1.25) while PTIME equals 1, and the decision of $D_2$ is again "YES", resulting in another ouput of data to the printhead 12 and the count of the data count register being reduced by 1. Of course the data count register is also being incremented by 1, at one millisecond intervals, as described in connection with FIG. 2 above. As indicated by the FIG. 3.a table for "TACH COUNT", "TIME" and "TIME−PTIME", the routine operation at 25 mm/sec. results in output of 1 piece of data for each of 4 tach pulses, and there is no output of data every 5th tach pulse. This is consistent with there being 5 tach pulses every 4 milliseconds, so that there are 4 outputs of data in 4 milliseconds, to maintain a constant time scale.

Figure 3B:
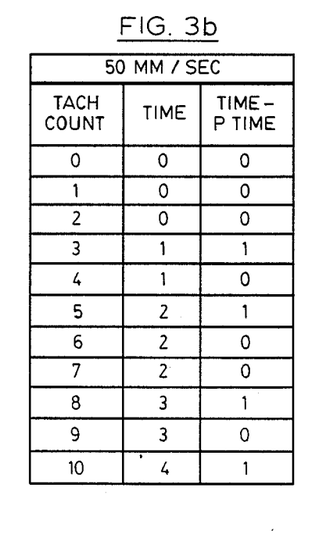
Figure 3C:
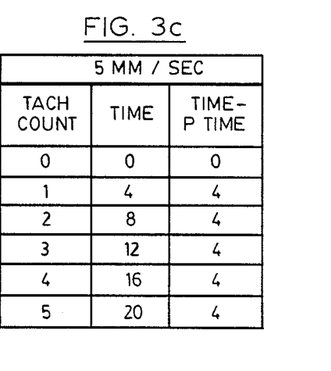

As illustrated by the tables for "TACH COUNT", "TIME" and "TIME−PTIME", in FIGS. 3.b and 3.c, the timing and amount of data outputted from the buffer memory means will result in a generally constant time scale for 50 mm/sec, and 5 mm/sec speeds, respectively, and for various other paper speeds which may be selected.

As will be apparent from the values shown in FIG. 3.c, at a speed of 5 mm/sec., which equates to 0.25 tachs per millisecond, for a tach count of 1, (TIME−PTIME) has a value of 4, indicating that 4 pieces of data will be "subtracted" from the data count register and buffer memory 20. Various arrangements could be utilized so that the output from the buffer memory transmitted to the printhead is representative of the 4 pieces of data, for example, outputting an average value of such data. In the preferred embodiment, the piece of data outputted to the printhead is determined by outputting from the buffer memory 20 a piece of data located at a point according to the value of the data count register, after subtraction of (TIME−PTIME), with the result being that 3 pieces of data are effectively skipped, while the 4th and last piece of data from the "FIFO" buffer memory is printed by the printhead 12. Although the resolution of the chart data is reduced at the speed of 5 mm/sec., a constant time scale is maintained since 20 pieces of data are accounted for upon a tach count of 5, which corresponds to 20 milliseconds, at the user selected 5 mm/sec. speed.

In other words, as previously described, if the data count exceeds the preselected value, 256, so that the motor speed and tach driven outputting of data is consistently behind in taking data out of the buffer memory 20, then the experience count register 26 is increased to an integer value of 1 or more so that the initial or current pulse widths are incremented by an additional unit or more to increase the motor speed. Accordingly, the speed at which data is outputted to printhead 12 increases to, in effect, match the one piece of data per millisecond provided from the analog to digital converter 18 to the buffer memory 20. Similarly, if the amount of the data stored in the buffer memory is less than 256, and outputting of data is consistently ahead of the preselected 256 value, then the initial pulse widths are reduced to reduce motor speed so that output of data from the buffer memory to the printhead slows, and again corresponds to the input of one piece of data per millisecond provided from the analog to digial converter 18 to the buffer memory 20.

While the operation of the logic routines as described in connection with FIGS. 2 and 3 tends to maintain a correct motor speed, it should be appreciated that provision of the buffer memory and the outputting of data at a rate proportional to the D.C. motor speed results in maintaining a constant time scale chart record, even in the event of temporary variations in the D.C. motor speed, as discussed above.

When the motor 30 is shut-off, the microcomputer 22 operates so that the data in the buffer memory is outputted. The accuracy of the data printout during motor shut-off is not of particular concern, given the generally extended time period during which the ECG signals are monitored during the normal D.C. motor operation at selected speeds, as described herein. The above described operations are repeated upon subsequent motor start-up.

Thus, it should be appreciated that the subject invention provides a method and an apparatus employing a D.C. motor and digital printhead wherein the speed of the D.C. motor is controlled in accordance with the amount of data stored in the buffer memory, so that the motor speed is increased if the buffer memory is storing more than a preselected amount of data, and so that the motor speed is decreased if the buffer memory is storing less than such preselected amount of data. At the same time, data is outputted from the buffer memory through the printhead for recording on a chart at a rate proportional to the speed of the D.C. drive motor, so as to maintain a generally constant time scale chart record regardless of temporary variations in motor speed, or the speed of the motor selected.

While the preferred embodiment has been described in connection with controlling a D.C. drive motor and digital printhead of an electrocardiogram, it should be appreciated by those skilled in the art that the invention provides a method and apparatus employing a D.C. drive motor and other means for supplying digital data for graphically recording other types of data on a constant time scale, regardless of temporary variances in the D.C. motor speed. Accordingly, while a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A method of controlling a D.C. drive motor and digital printhead of an electrocardiogram to produce a chart record at a constant time scale regardless of temporary variations in the preselected nominal D.C. drive motor speed comprising:

storing sensed digital ECG data by means of a buffer memory;

controlling the speed of the D.C. drive motor in accordance with the amount of data stored in the buffer memory, so that the motor speed is increased if the buffer memory is storing more than a preselected amount of data, and so that motor speed is decreased if the buffer memory is storing less than the preselected amount of data; and outputting ECG data from the buffer memory to the printhead for recording at a rate proportional to the speed of the D.C. drive motor, so as to produce a constant time scale chart record of such data regardless of temporary variations in the D.C. drive motor speed.

2. A method in accordance with claim 1 wherein the steps for controlling the speed of the D.C. drive motor are further defined as utilizing a data count register and a pulse width register, and adjusting the data count to have a count indicative of the amount of data contained in the buffer memory, and controlling the pulse width register to effect generation of, during a given time interval, a long pulse to energize the D.C. motor if the count of the data count register is greater than a preselected value, corresponding to the buffer memory storing more than said preselected amount of data, or a short pulse to energize the D.C. motor if the count of the data count register is less than said preselected value.

3. A method in accordance with claim 2 wherein the step for controlling the speed of the D.C. drive motor is further defined as utilizing an experience count register, and incrementing by a fractional value the experience count register each time a long pulse is generated, and decrementing by a fractional value the experience count register each time a short pulse is generated and, when the experience count register reaches a positive integer value, adjusting the pulse width register to increase the width of the long and short pulses generated, to increase the speed of the D.C. motor, and when the experience count register reaches a negative value, adjusting the pulse width register to decrease the width of the long and short pulses generated, to decrease the D.C. motor speed.

4. A method in accordance with claim 3 wherein the step of adjusting the data count register is further defined as incrementing the count of the data count register in response to a piece of data being added and stored in the buffer memory per a given unit of time, and wherein the step of outputting data is further defined as utilizing a tach count register and incrementing the count in the tach count register upon the occurrence of a tach pulse generated by the D.C. motor, and calculating upon the occurrence of a tach pulse a numerical "TIME" value equal to the count in the tach count register, divided by the number of tach pulses per such given unit of time, the quotient being rounded to the smallest whole number value, and determining if "TIME" is greater than "PTIME," where "PTIME" is equal to the immediately preceding value of "TIME" prior to the tach count register being incremented by an additional tach pulse, and if TIME is greater than PTIME, subtracting (TIME−PTIME) from the value of the data count register and outputting data from the buffer memory to the printhead for recording.

5. A method in accordance with claim 4 wherein the step of outputting data from the buffer memory is further defined as outputting from the buffer memory to the printhead for recording a piece of data located in the buffer memory at a point corresponding to the resulting count of the data count register after subtraction of (TIME−PTIME).

6. A method in accordance with claim 2 wherein the step of adjusting the data count register is further defined as incrementing the count of the data count register in response to a piece of data being added and stored in the buffer memory per a given unit of time, and wherein the step of outputting data is further defined as utilizing a tach count register, and incrementing the count in the tach count register upon the occurrence of a tach pulse generated by the D.C. motor, and calculating upon the occurrence of a tach pulse a numerical "TIME" value equal to the count in the tach count register, divided by the number of tach pulses per such given unit of time, the quotient being rounded to the smallest whole number, and determining if "TIME" is greater than "PTIME," where "PTIME" is equal to the immediately preceding value of "TIME" prior to the tach count register being incremented by an additional tach pulse, and if TIME is greater than PTIME, subtracting (TIME−PTIME) from the value of the data count register and outputting data from the buffer memory to the printhead for recording.

7. A method in accordance with claim 6 wherein the step of outputting data from the buffer memory is further defined as outputting from the buffer memory to the printhead for recording a piece of data located in the buffer memory at a point corresponding to the resulting count of the data count register after subtraction of (TIME−PTIME).

8. A method of controlling a D.C. drive motor and the supplying of digital data to the chart of a recorder to produce a constant time scale chart record regardless of temporary variations in the preselected nominal D.C. drive motor speed comprising:

storing sensed digital data by means of a buffer memory;

controlling the speed of the D.C. drive motor in accordance with the amount of data stored in the buffer memory, so that the motor speed is increased if the buffer memory is storing more than a preselected amount of data, and so that motor speed is decreased if the buffer memory is storing less than the preselected amount of data; and outputting sensed data from the buffer memory and supplying such data to the chart at a rate proportional to the speed of the D.C. drive motor, so as to produce a constant time scale chart record of such data regardless of temporary variations in the D.C. drive motor speed.

9. A method in accordance with claim 8 wherein the steps for controlling the speed of the D.C. drive motor are further defined as utilizing a data count register and a pulse width register, and adjusting the data count register to have a count indicative of the amount of data contained in the buffer memory, and controlling the pulse width register to effect generation of, during a given time interval, a long pulse to energize the D.C. motor if the count of the data count register is greater than a preselected value, corresponding to the buffer memory storing more than said preselected amount of data, or a short pulse to energize the D.C. motor if the count of the data count register is less than said preselected value.

10. A method in accordance with claim 9 wherein the step for controlling the speed of the D.C. drive motor is further defined as utilizing an experience count register, and incrementing by a fractional value the experience count register each time a long pulse is generated, and decrementing by a fractional value the experience count register each time a short pulse is generated and, when the experience count register reaches a positive integer value, adjusting the pulse width register to increase the width of the long and short pulses generated, to increase the speed of the D.C. motor, and when the experience count register reaches a negative value, adjusting the pulse width register to decrease the width of the long and short pulses generated, to decrease the D.C. motor speed.

11. A method in accordance with claim 9 wherein the step of adjusting the data count register is further defined as incrementing the count of the data count register in response to a piece of data being added and stored in the buffer memory per a given unit of time, and wherein the step of outputting data is further defined as utilizing a tach count register and incrementing the count in the tach count register upon the occurrence of a tach pulse generated by the D.C. motor, and calculating upon the occurrence of a tach pulse a numerical "TIME" value equal to the count in the tach count register, divided by the number of tach pulses per such given unit of time, the quotient being rounded to the smallest whole number value, and determining if "TIME" is greater than "PTIME," where "PTIME" is equal to the immediately preceding value of "TIME" prior to the tach count register being incremented by an additional tach pulse, and if TIME is greater than PTIME, subtracting (TIME−PTIME) from the value of the data count register and outputting data from the buffer memory to the printhead for recording.

12. A method in accordance with claim 11 wherein the step of outputting data from the buffer memory is further defined as outputting from the buffer memory for recording a piece of data located in the buffer memory at a point corresponding to the resulting count of the data count register after subtraction of (TIME−PTIME).

13. A method in accordance with claim 9 wherein the step of adjusting the data count register is further defined as incrementing the count of the data count register in response to a piece of data being added and stored in the buffer memory per a given unit of time, and wherein the step of outputting data is further defined as utilizing a tach count register and incrementing the count in the tach count register upon the occurrence of a tach pulse generated by the D.C. motor, and calculating upon the occurrence of a tach pulse a numerical "TIME" value equal to the count in the tach count register, divided by the number of tach pulses per such given unit of time, the quotient being rounded to the smallest whole number value, and determining if "TIME" is greater than "PTIME," where "PTIME" is equal to the immediately preceding value of "TIME" prior to the tach count register being incremented by an additional tach pulse, and if TIME is greater than PTIME, subtracting (TIME−PTIME) from the value of the data count register and outputting data from the buffer memory to the printhead for recording.

14. A method in accordance with claim 13 wherein the step of outputting data from the buffer memory is further defined as outputting from the buffer memory for recording a piece of data located in the buffer memory at a point corresponding to the resulting count of the data count register after subtraction of (TIME−PTIME).

15. A method of controlling a D.C. drive motor and digital printhead of an electrocardiogram to produce a chart record at a constant time scale regardless of temporary variations in the preselected nominal D.C. drive motor speed comprising:
storing sensed digital ECG data;
controlling the speed of the D.C. drive motor in accordance with the amount of the ECG data stored, so that the motor speed is increased if the amount of data stored is more than a preselected amount of data, and so that motor speed is decreased if the amount of data stored is less than the preselected amount of data; and
outputting ECG data to the printhead for recording at a rate proportional to the speed of the D.C. drive motor, so as to produce a constant time scale chart record of such data regardless of temporary variations in the D.C. drive motor speed.

16. A method in accordance with claim 15 wherein the step of controlling the speed of the D.C. drive motor is further defined as generating, during a given time interval, a long pulse to energize to D.C. motor if the amount of data stored is greater than said preselected amount of data, and a short pulse to energize the D.C. motor if the amount of data stored is less than said preselected amount of data.

17. A method in accordance with claim 16 wherein the step of generation of long and short pulses is further defined as determining the number of long and short pulses generated, and when the number of long pulses generated exceeds the number of short pulses generated by a given value, increasing the width of the long and short pulses generated, to increase the D.C. motor speed, and when the number of short pulses generated exceed the number of long pulses generated, decreasing the width of the long and short pulses generated to decrease the D.C. motor speed.

18. Apparatus employing a D.C. drive motor and digital printhead for recording electrocardiographic data on a chart at a constant time scale, regardless of temporary variations in the preselected nominal D.C. drive motor speed, comprising:
buffer memory means for storing sensed digital ECG data, including a preselected amount of data;
means for controlling the speed of the D.C. drive motor in accordance with the amount of data stored in said buffer memory means, so that the motor speed is increased if the buffer memory means is storing more than said preselected amount of data, and so that motor speed is decreased if the buffer memory means is storing less than said preselected amount of data; and means for outputting ECG data from the buffer memory means to the digital printhead for recording at a rate proportional to the speed of the D.C. drive motor, so as to produce a constant time scale chart record of said data regardless of temporary variations in the D.C. drive motor speed.

19. Apparatus in accordance with claim 15 wherein said speed controlling means comprises data count register means having a count indicative of the amount of data contained in said buffer memory means, and pulse width register means for controlling generation of, during a given time interval, a long pulse to energize the D.C. motor if the count of said data count register means is greater than a preselected value, corresponding to said buffer memory means storing more than said preselected amount of data, or a short pulse to energize the D.C. motor if the count of said data count register means is less than said preselected value.

20. An apparatus in accordance with claim 19 wherein said speed controlling means further comprises experience count register means having a count incremented by a fractional value each time one of said long pulses is generated, said count being decremented by a fractional value each time one of said short pulse is generated, said experience count register means being operable, upon reaching a positive integer value, for causing said pulse width register means to increase the width of said long and short pulses generated to increase the speed of the D.C. drive motor, and operable, upon reaching a negative value, for causing said pulse width register to decrease the width of said long and short pulses generated to decrease the D.C. drive motor speed.

21. An apparatus in accordance with claim 20 wherein the count of said data count register means is incremented in response to a piece of data being added and stored in said buffer memory means per a given unit of time, and wherein said means for outputting ECG data comprises tach count register means having a count incremented upon the occurrence of a tach pulse generated by the D.C. motor, means for calculating a numerical "TIME" value equal to the count in said tach count register means divided by the number of tach counts per said given unit of time, the quotient being rounded to the smallest whole number value, and means for determining if "TIME" is greater than "PTIME," where the value of "PTIME" is set to the immediately preceding value of "TIME" before the tach count register is incremented by the occurrence of an additional tach pulse, and means, if TIME is greater than PTIME, for subtracting (TIME−PTIME) from the value of the data count register means and outputting data from said buffer memory means to the printhead for recording.

22. An apparatus in accordance with claim 21 wherein said means for outputting data from said buffer memory means is operable for outputting from said buffer memory means to the printhead for recording a piece of data located in said buffer memory means at a point corresponding to the resulting count of said data count register means after subtraction of (TIME−PTIME).

23. An apparatus in accordance with claim 19 wherein the count of said data count register is incremented in response to a piece of data being added and stored in said buffer memory means per a given unit of time, and wherein said means for outputting ECG data comprises tach count register means having a count incremented upon the occupance of a tach pulse generated by the D.C. motor, and means for calculating a numerical "TIME" value equal to the count in said tach count register means divided by the number of tach counts per said given unit of time, the quotient being rounded to the smallest whole number value, and means for determining if "TIME" is greater than "PTIME," where the value of "PTIME" is set to the immediately preceding value of "TIME" before the tach count register is incremented by the occurrence of an additional tach pulse, and means, if TIME is greater than PTIME, for subtracting (TIME−PTIME) from the value of the data count register means and outputting data from said buffer memory means to the printhead for recording.

24. An apparatus in accordance with claim 23 wherein said means for outputting data from said buffer memory means is operable for outputting from said buffer memory means to the printhead for recording a piece of data located in said buffer memory means at a point corresponding to the resulting count of said data count register means after subtraction of (TIME−PTIME).

25. Apparatus employing a D.C. drive motor and means for supplying digital data for recording on a chart at a constant time scale, regardless of temporary variations in the preselected nominal D.C. drive motor speed, comprising:

buffer memory means for storing the digital data, including a preselected amount of data;

means for controlling the speed of the D.C. drive motor in accordance with the amount of data stored in said buffer memory means, so that the motor speed is increased if the buffer memory means is storing more than said preselected amount of data, and so that motor speed is decreased if the buffer memory means is storing less than said preselected amount of data; and means for outputting data from the buffer memory means to the means for supplying digital data for recording at a rate proportional to the speed of the D.C. motor, so as to produce a constant time scale chart record of said data regardless of temporary variations in the D.C. drive motor speed 26. Apparatus in accordance with claim 25 wherein said speed controlling means comprises data count register means having a count indicative of the amount of data contained in said buffer memory means, and pulse width register means for controlling generation of, during a given time interval, a long pulse to energize the D.C. motor if the count of said data count register means is greater than a preselected value, corresponding to said buffer memory means storing more than said preselected amount of data, or a short pulse to energize the D.C. motor if the count of said data count register means is less than said preselected value.

27. An apparatus in accordance with claim 26 wherein said speed controlling means further comprises experience count register means having a count incremented by a fractional value each time one of said long pulses is generated, said count being decremented by a fractional value each time one of said short pulse is generated, said experience count register means being operable, upon reaching a positive integer value, for causing said pulse width register means to increase the width of said long and short pulses generated to increase the speed of the D.C. drive motor, and operable, upon reaching a negative value, for causing said pulse width register to decrease the width of said long and short pulses generated to decrease the D.C. drive motor speed.

28. An apparatus in accordance with claim 27 wherein the count of said data count register means is incremented in response to a piece of data being added and stored in said buffer memory means per a given unit of time, and wherein said means for outputting ECG data comprises tach count register means having a count incremented upon the occurrence of a tach pulse generated by the D.C. motor, means for calculating a numerical "TIME" value equal to the count in said tach count register means divided by the number of tach counts per said given unit of time, the quotient being rounded to the smallest whole number value, and means for determining if "TIME" is greater than "PTIME," where the value of "PTIME" is set to the immediately preceding value of "TIME"before the tach count register is incremented by the occurrence of an additional tach pulse, and means, if TIME is greater than PTIME, for subtracting (TIME−PTIME) from the value of the data count register means and outputting data from said buffer memory means to the means for supplying digital data for recording.

29. An apparatus in accordance with claim 28 wherein said means for outputting data from said buffer memory means is operable for outputting from said buffer memory means to the means for supplying digital data for recording a piece of data located in said buffer memory means at a point corresponding to the resulting count of said data count register means after subtracting of (TIME−PTIME).

30. An apparatus in accordance with claim 26 wherein the count of said data count register means is incremented in response to a piece of data being added and stored in said buffer memory means per a given unit of time, and wherein said means for outputting ECG data comprises tach count register means having a count incremented upon the occurrence of a tach pulse generated by the D.C. motor, and means for calculating a numerical "TIME" value equal to the count in said tach count register means divided by the number of tach counts per said given unit of time, the quotient being rounded to the smallest whole number value, and means for determining if "TIME" is greater than "PTIME," where the value of "PTIME" is set to the immediately preceding value of "TIME" before the tach register is incremented by the occurrence of an additional tach pulse, and means, if TIME is greater than PTIME, for subtracting (TIME−PTIME) from the value of the data count register means and outputting data from said buffer memory means to the means for supplying digital data for recording.

31. An apparatus in accordance with claim 30 wherein said means for outputting data from said buffer memory means is operable for outputting from said buffer memory means to the means for supplying digital data for recording a piece of data located in said buffer memory means at a point corresponding to the resulting count of said data count register means after substation of (TIME−PTIME).

* * * * *

UNITED STATES PATENT AND TRADEMARK OFFICE
CERTIFICATE OF CORRECTION

PATENT NO. : 4,951,681

DATED : August 28, 1990

INVENTOR(S) : David W. Mortara

It is certified that error appears in the above-identified patent and that said Letters Patent is hereby corrected as shown below:

Column 10, line 23, cancel "2" and insert -- 3 --;

Column 14, line 45, after "speed" insert a period (.);

Column 16, line 30, cancel "substation" and insert -- subtraction --.

Signed and Sealed this

Twenty-second Day of January, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,951,681
DATED : August 28, 1990
INVENTOR(S) : DAVID W. MORTARA

It is certified that error appears in the above—identified patent and that said Letters Patent is hereby corrected as shown below:

Column 10, Line 36, after "number" and before the comma, insert -- value --;

Column 13, Line 44, before "means" insert -- and --

Column 14, Line 3, cancel "occupance" and insert --occurrence--.

Signed and Sealed this

Fourth Day of August, 1992

Attest:

DOUGLAS B. COMER

*Attesting Officer*  *Acting Commissioner of Patents and Trademarks*